United States Patent [19]

Dove

[11] Patent Number: 5,691,446
[45] Date of Patent: Nov. 25, 1997

[54] METHODS FOR REDUCING ALLERGENICITY OF NATURAL RUBBER LATEX ARTICLES AND ARTICLES SO PRODUCED

[76] Inventor: Jeffrey S. Dove, 19342 Gateway, Santa Ana, Calif. 92705

[21] Appl. No.: 519,371

[22] Filed: Aug. 25, 1995

[51] Int. Cl.$^6$ .......................... C08F 34/00; C08F 134/00
[52] U.S. Cl. ...................... 528/935; 528/934; 526/295
[58] Field of Search ..................... 528/934, 935; 526/295

[56] References Cited

U.S. PATENT DOCUMENTS

| | | | |
|---|---|---|---|
| 3,248,245 | 4/1966 | Hodge | 106/125 |
| 3,280,065 | 10/1966 | Langner | 524/47 |
| 3,872,515 | 3/1975 | Miner et al. | 2/168 |
| 4,218,779 | 8/1980 | Hart et al. | 2/168 |
| 4,238,685 | 12/1980 | Beede et al. | 522/1 |
| 4,463,156 | 7/1984 | McGary, Jr. et al. | 528/65 |
| 4,482,577 | 11/1984 | Goldstein et al. | 427/2 |
| 4,526,828 | 7/1985 | Fogt et al. | 428/229 |
| 4,548,844 | 10/1985 | Podell et al. | 428/35 |
| 5,014,362 | 5/1991 | Tillotson et al. | 2/168 |
| 5,019,601 | 5/1991 | Allen | 523/123 |
| 5,069,965 | 12/1991 | Esemplare | 428/330 |
| 5,088,125 | 2/1992 | Ansell et al. | 2/167 |
| 5,089,205 | 2/1992 | Huang et al. | 264/255 |
| 5,126,334 | 6/1992 | Fitt et al. | 514/60 |
| 5,138,719 | 8/1992 | Orlianges et al. | 2/168 |

*Primary Examiner*—Nathan M. Nutter
*Attorney, Agent, or Firm*—Bruce Canter Kurt, MacLean, Oppenheimer, Poms

[57] ABSTRACT

Reduced allergenicity natural rubber latex articles having otherwise normal physical, mechanical, and chemical properties are produced by inducing the antigenic components of the natural rubber latex to bloom onto and adjacent to the tissue contacting surface of the article prior to treatment with a screening reagent to sequester the antigenic regions.

20 Claims, No Drawings

METHODS FOR REDUCING ALLERGENICITY OF NATURAL RUBBER LATEX ARTICLES AND ARTICLES SO PRODUCED

FIELD OF THE INVENTION

The present invention relates in general to methods for producing latex articles formed of natural rubber. More particularly, the present invention is directed to methods for producing natural rubber latex articles having tissue contacting surfaces whose antigenic components are fixed to one another without altering or degrading the molecular structure of the latex material itself. In this manner, the present invention is able to produce latex articles possessing the beneficial chemical, physical, and mechanical properties of natural rubber latex while significantly reducing harmful immunologic reactions in hypersensitive individuals and minimizing the risk of inadvertent sensitization of unsensitized individuals coming into contact with the surfaces of the devices and article so produced. Moreover, the methods of the present invention are non-hazardous and readily applicable to existing latex article manufacturing procedures and uses.

BACKGROUND OF THE INVENTION

One of the earliest known elastomeric polymers, natural rubber latex has long been utilized in a wide variety of commercial and consumer products ranging from automobile tires to sophisticated medical devices. Cured from the milky sap collected from diverse plant sources including desert shrubs and tropical trees, the most common source of natural rubber latex is the Brazilian rubber tree, *Hevea brasiliensis*. Currently, it is estimated that nearly 40,000 products contain natural rubber latex. Of these, several hundred possess medical utilities including use as surgical or examination gloves, catheters, and bandages. Natural rubber latex products exhibit a number of beneficial properties including resistance to creep (undesirable material elongation under constant stress) and compression resistance (the ability to return to original size and volume after squeezing). Additionally, being derived in large volume from natural sources, they are readily available and relatively inexpensive to manufacture and use.

Unfortunately, natural rubber latex has one serious drawback. An estimated seventeen million people in the United States alone are allergic to it. The cured rubbers produced from natural rubber latex contain naturally occurring emulsifying proteins and other biopolymers with antigenic components that make some people itch and others burn with rashes. Some highly sensitive individuals can be sent into life-threatening anaphylactic shock with a mere touch.

Because this natural rubber latex allergic hypersensitivity develops only after some initial sensitizing contact with natural rubber latex, health care workers were one of the first populations recognized to be at risk. A growing number of mechanical supplies and products including surgical gloves, elastic bandages, adhesive tape, blood-pressure cuffs, and catheters are the common sources of exposure. Similarly, many consumer products also utilize natural rubber latex, most notably, kitchen gloves and condoms. Recently, some researchers have identified airborne microparticles of worn automobile and truck tires contained in roadside dust as an additional source of natural rubber latex exposure and subsequent development of hypersensitivity.

Although first reported in the 1930s, the severity and number of natural rubber latex allergy cases has increased dramatically in the last decade. At present, the most popular explanations for the sudden up-turn in allergic reactions are the increased exposure to natural rubber latex gloves resulting from the AIDS epidemic as well as an industry-wide modification in the production methodology of natural rubber latex articles in an effort to reduce resultant water pollution. These changes in production methodology have eliminated zinc salts used in the coagulation of the latex as a source of water pollution but may have inadvertently increased the allergenicity of the natural rubber latex articles so produced. In 1982, the Federal Food and Drug Administration issued an alert regarding the allergenicity of natural rubber latex products, originally believing that antioxidant preservatives and other metal containing compounds utilized in their production were the source of the reaction. Currently, those skilled in the art suspect that natural proteins and biopolymers embedded in the latex are the prime antigenic candidates responsible for inducing allergic reactions.

The earliest and most simple efforts at reducing natural rubber latex allergenicity involved washing pre-treatment of the harvested latex sap with water and detergents to solubilize and extract these antigenic protein components. Natural rubber latex sap is an oil-in-water emulsion of pure cis-(polyisoprene), a naturally occurring plant polymer. As harvested, this natural rubber polymer is suspended in the water based emulsion by a group of naturally occurring surfactant and detergent type plant proteins. Mixing the natural emulsion with excess water, or a combination of water and synthetic detergents or digestive enzymes, followed by centrifugation to separate out the coagulated natural surfactant and detergent proteins effectively decreases the total number of allergenic proteins in the natural raw material. As a result, latex articles produced from the washed emulsions exhibit reduced antigenicity and allergenic properties. Alternatively, during the manufacturing process, some manufacturers include additional water or chemical extraction and washing steps to pull any remaining, loosely bound antigenic proteins from the natural rubber latex material.

Both of these washing procedures are effective at removing sources of antigenicity and at reducing resultant allergic responses. They are relatively inexpensive to implement as well. However, significant quantities of antigenic components remain in the latex articles treated with these prior art washing procedures. Moreover, while applicable to large scale bulk material processing and to the production of relatively unsophisticated articles, these techniques are not particularly suitable for the production of reduced allergenicity precision made products and to products that remain in direct contact with individuals for extended periods of time. Precision made or complex products are not easily washed and their production processes cannot be interrupted with additional handling steps and delays. Extended use products may possess sufficient residual antigenic properties to trigger allergic reactions following lengthy exposure.

In some circumstances, it may be possible to pre-treat the natural rubber latex emulsions with chemical agents that will salt out or denature the suspended surfactant compounds, thereby reducing their antigenicity. Unfortunately, these chemical treatments also may affect the latex itself. As a result, articles formed from such pre-treated materials may exhibit inferior physical, chemical, and mechanical properties, and may be more suspectable to oxidative degradation relative to untreated, though allergenic, latex articles. Compounding matters, in the heavily regulated medical industry, these chemically modified materials may be sufficiently different from existing, approved materials to require expensive regulatory approval prior to their marketing and use.

A successful, yet expensive, alternative technique for avoiding natural rubber latex hypersensitivity is to substitute artificial or synthetic latex materials in place of the natural rubber latex. Latex water emulsions of synthetic rubber or plastics obtained by polymerization enable manufacturers to precisely tailor the content of the emulsions in order to eliminate antigenic components. These synthetic latexes are particularly useful in coatings, paints and adhesives. Condoms and rubber gloves have been developed from synthetic rubber latexes that, at present, do not induce a natural rubber latex-like hypersensitivity response in sensitized individuals. Unfortunately, these synthetic materials are significantly more expensive than natural rubber latex. More importantly, their physical and mechanical properties are inferior in many applications. Some artificial rubbers lack sufficient elasticity or strength to function effectively as gloves. Others exhibit material creep when subjected to constant stress which results in sagging and bagginess that may interfere with their operability. Others possess poor compression resistance and yield to compressive stress.

An acceptable middle ground has been developed in some circumstances through coating processes that isolate the surfaces of the natural rubber latex articles with nonallergenic materials such as polyurethane. These techniques generally retain the beneficial mechanical properties of the underlying natural rubber latex and hide the allergenic natural protein components to prevent hypersensitive individuals from reacting. Though effective, coating technologies are not without their attendant drawbacks. By adding additional processing or manufacturing steps and expensive synthetic materials, they significantly increase the costs associated with the production of coated products. Though seemingly stable, coatings may not provide permanent hypoallergenicity as cracking, peeling or abrasion during use still may allow the underlying natural latex to be exposed to sensitive individuals. This is particularly true for inflatable latex balloons where differential expansion rates between the underlying latex and the coating may cause the latex to be exposed.

Even more recently, some researchers have identified nonallergenic natural rubber latex produced from alternative plant sources. For example, a wild desert shrub, *Parthenium argentatum*, reportedly produces a natural rubber latex sap lacking the allergy causing proteins present in sap derived from the Brazilian rubber tree. Though promising, these alternative sources may require genetic manipulation to increase their rubber formation to a point where they will be effective competitors for the Brazilian rubber tree. It is also suspected that they may contain their own surfactant and detergent type plant proteins that will ultimately induce hypersensitivity responses in exposed individuals over time following widespread application.

Accordingly, one of the primary objectives of the present invention is to provide effective methods for reducing the allergenicity of natural rubber latex products that can be incorporated into existing manufacturing processes without significant modification or expense.

It is an additional objective of the present invention to provide methods for reducing the allergenicity of natural rubber latex articles that do not involve coating or grafting additional polymers onto the surfaces of the articles.

It is a still further objective of the present invention to provide methods for reducing the allergenicity of natural rubber latex articles that do not significantly change the natural rubber polymers nor alter their chemical, physical, and mechanical properties.

Concomitant with each of the foregoing objects is the objective of producing reduced allergenicity, natural rubber latex articles themselves which exhibit the normally expected ranges of beneficial physical, mechanical, and chemical properties for such articles.

SUMMARY OF THE INVENTION

Generally stated, these and other objects are achieved by the present invention which provides methods for producing natural rubber latex articles and devices that are significantly hypoallergenic. Without changing or reacting with the principal polymeric components of the cured natural rubber latex material, the methods of the present invention selectively neutralize the reactivity of the naturally occurring antigenic surfactant and detergent type plant proteins present on and adjacent to the surface of the cured latex material by inducing the blooming of the antigenic components to the surfaces intended to come into contact with an individual. In this manner, all of the beneficial properties and aspects of natural rubber latex are maintained while the antigenic sites on the exposed surfaces of the materials are rendered virtually inert to the body's immune system.

More particularly, the methods of the present invention are useful for the production of "hypo" or reduced allergenic natural rubber latex articles and devices which maintain the normal and desirable physical, mechanical, and chemical properties of unmodified natural rubber latex. The methods of the present invention are simple, inexpensive, non-hazardous, and readily applicable to existing latex article manufacturing and processing steps with minimal impact other than the beneficial reduction in surface allergenicity. In a broad aspect, the present invention produces natural rubber latex articles having reduced allergenicity through the steps of inducing the naturally occurring antigenic components of natural rubber latex to bloom onto or adjacent to at least one of the latex article tissue contacting surfaces and then treating these bloomed antigenic components with one or more screening reagents which chemically interact with the various functional groups found along the chemical backbone of the bloomed antigenic components in a linking reaction which sequesters or otherwise covers up the antigenic regions of the target components.

An exemplary embodiment of the production methodology of the present invention begins with the provision of a natural rubber latex emulsion which includes the naturally occurring antigenic surfactant-type molecules. From this emulsion, a latex article having at least one surface intended to contact a patient's tissue is formed. The blooming of the antigenic components onto and adjacent this intended tissue contacting surface is induced, for example by coagulation of the latex emulsion into a gel on an article forming mandrel and displacing the antigenic components toward the exposed surface of the gel. Chemical treatment of the bloomed antigenic components with the screening reagent can be accomplished through a variety of relatively mild chemical procedural steps including dipping in treatment baths containing effective concentrations of one or more screening reagents under suitable reaction conditions of temperature and pH for a sufficient period of time to substantially complete the screening reaction. Any unreacted screening reagent can be removed through washing along with any other water soluble components remaining in the latex article.

Alternatively, following formation of the coagulated gelatinous natural rubber latex emulsion on the article forming mandrel, the gel can be dried and cured in a conventional manner prior to treatment with screening reagent. The cured gel will continue to express the bloomed antigenic components at its surface so that the chemical treatment can effectively sequester the antigenic regions of these components without changing the underlying natural rubber polymer.

Those skilled in the art will appreciate that the methods of the present invention may be applied to virtually all normal latex article production steps as long as the appropriate concern is directed to avoiding obvious, undesired reactions with vulcanization and antioxidant chemicals that normally may be present during latex article production. For example, the natural rubber latex emulsion itself can be treated to reduce allergenic protein by selecting one or more screening reagents having appropriate partition coefficients to induce blooming of the antigenic components at the emulsion interfaces simultaneously with their chemical treatment. Proper selection of the screening reagent's chemical properties can avoid any undesired reactions with additional components of the emulsions. Alternatively, the emulsions can be coagulated onto forming mandrels which have been pretreated with a surface layer of screening reagent prior to latex dipping. The methods of the present invention may also be applied to later stage production sets. For example, screening reagents can be added to release coating formulations or donning coating formulations to produce powder free formed latex articles. If desired, the features of the screening reagents can be incorporated into subsequent polymer coating chemistry so that sequestration and coating of the antigenic regions can occur simultaneously. It is also contemplated as being within the scope of the present invention to treat both sides of a latex article. Thus, the first bloomed surface can be treated with screening reagent in any of the previously discussed steps. Then, the opposite surface can be treated with one of the later stage techniques.

Similarly, though it is preferred that the methods of the present invention be utilized in conjunction with aqueous solutions, where appropriate, non-aqueous solutions may be utilized within the scope and teaching thereof. As a result, the methods of the present invention impart minimal impact to normal manufacturing procedures, and may be utilized to treat raw latex, processed latex compounds, prevulcanized latex compounds, vulcanized articles, and finished latex articles, as desired.

Screening reagents that may be utilized to practice the present invention include a wide variety of chemical agents that will react with one or more of the various functional groups found along the antigenic component molecules under conditions that are sufficiently mild to avoid significant interaction with the associated latex rubber or desireable emulsion components. As an added feature of the present invention, the partition coefficient of the screening reagents may be modified to harmonize or match the hydrophobic/hydrophilic character of the target antigenic components, or at least their antigenic regions, to enhance their screening effectiveness while improving their processing performance and further reducing their interaction with the underlying latex and emulsion components.

Exemplary screening reagents include multifunctional chemical agents and particularly difunctional agents such as diepoxies, dialdehydes, dienes, bismalimides, and diisocyanates, though additional multi- and difunctional analogs and even monofunctional chemical agents are contemplated as being within the scope of the present invention. Moreover, side chains having detergent-like character may be attached to the screening reagents to modify their partition coefficients. Similarly, attaching large or bulky side chains to mono- or difunctional screening reagents also enhances their screening ability. Oligimers and low molecular weight polymers containing appropriately configured functional groups also may be employed.

Regardless of the screening reagent utilized, it is preferred that the treating conditions be relatively mild. Accordingly, reaction temperatures should be sufficient to induce chemical reaction of the screening reagent with the antigenic component without attacking the latex molecules. Temperatures ranging from 20° C. to 100° C. have been found to be appropriate for this purpose. Similarly, treatment pH should be appropriate to drive the desired reactions forward but not so extreme to drive undesired reactions. Exemplary treatment pHs range from 9 pH units to 12 pH units. Reaction times ranging from 1 minute to 30 minutes are also appropriate as they do not significantly impact existing manufacturing protocols with unnecessary delays or complexity. Effective concentrations of screening reagents may range from 0.1 weight percent (wt %) to 10 wt % in aqueous or non-aqueous solutions as these concentrations are generally non-hazardous, non-toxic, inexpensive and easy to use.

Because the methods of the present invention are readily applicable to existing latex production techniques and methodology, the present invention is able to produce virtually any latex article or device with the added benefit of having one or more tissue contacting surfaces that exhibit significantly reduced allergenicity. These articles include surgical and examination gloves, condoms, catheters, catheter inflation and occlusion balloons, bandages, and more.

Further objects, features and advantages of the hypoallergenic natural rubber latex articles and manufacturing methods of the present invention, as well as a better understanding thereof, will be afforded to those skilled in the art from a consideration of the following detailed explanation of exemplary embodiments.

DETAILED DESCRIPTION OF EXEMPLARY EMBODIMENTS

The "hypoallergenic" or reduced allergenicity natural rubber latex articles of the present invention are intended for use in place of virtually any natural rubber latex article in order to reduce the incidence of latex sensitivity and allergic reaction experienced in the population at large. However, as those skilled in the art will appreciate, those circumstances where direct tissue contact with latex articles is experienced are the most likely targets for the significant benefits achieved with the present invention. Thus, the hundreds of medical devices, materials, and articles presently known may demonstrate the significant benefits of the present invention most clearly.

In today's medical environments, medical personnel often where latex gloves for hours on end. Dermatitis and more troublesome allergic responses to the skin of their hands can result from this constant contact with the internal glove surfaces. Similarly, allergic responses can be induced in medical patients and others routinely exposed to the external surfaces of the gloves. Even more significantly, medical patients, particularly cardiac patients, may be exposed to intimate latex-to-tissue contact for extended periods of time in connection with indwelling cardiac monitoring devices. Here, allergic reactions can be devastating.

For example, the commonly used Swan-Ganz catheter for monitoring cardiac performance may remain in a patient for periods of 8 to 72 hours. The inflatable latex balloons utilized to advance these catheters into the cardiac vasculature and to occlude individual arteries for pressure monitoring purposes come into direct contact with the delicate tissues lining the patient's vasculature. This long term, intimate tissue contact may be one of the most severe forms of latex exposure where the benefits of the present invention are most pronounced. Because synthetic latex inflation balloons cannot match the physical, mechanical, and chemical properties normally occurring in natural rubber latex balloons, they have not been able to function as effective substitutes for natural rubber latex in this critical physical environment.

Accordingly, without limiting the scope of present invention, exemplary embodiments thereof will be discussed in the context of exemplary medical inflation balloons and latex sheets or gloves because these articles are uniquely illustrative of the principles and benefits of the present invention. However, it should be emphasized that the present invention is not limited to inflation balloons, sheets, or gloves, and is widely applicable to virtually any article, device, or composition formed of latex.

With the appropriate understanding of the broad scope of the present invention, catheter inflation balloons provide a very clear demonstration of the beneficial and desirable physical, chemical, and mechanical properties normally present in natural latex articles. In contrast to natural rubber, synthetic rubber latex balloons formed of poly-isoprene and poly-butadiene are known to exhibit "creep" where the rubber material continues to elongate under constant stress. Following inflation and stretching, artificial rubber balloons may elongate up to 50% over their original dimensions. The resultant bagginess may cause functional problems upon withdrawal of the associated cardiac catheter if the sagging balloon material engages delicate internal structures. Additionally, synthetic balloons also exhibit compression resistance properties that are inferior to those normally present in natural rubber latex balloons. Under constant compressive stress such as that which may occur during folding, shipping, or storage, these materials can become permanently deformed and take a distorted "set" which may adversely affect their function.

Product shipping and storage conditions emphasize another beneficial property normally associated with natural rubber latex. When properly manufactured with the appropriate antioxidant compounds, articles formed of natural rubber latex resist aging and can be stored for significant periods of time without performance degradation. Thus, the elastic modulous, burst pressure, and number of inflation cycles before failure of natural rubber latex balloons remains relatively constant during storage. This storage capability enhances the utility of such products and contributes to their relatively low cost when contrasted to synthetic rubber devices.

Natural rubber latex is also chemically resistant to both acids and bases and, in most circumstances, can be considered chemically inert. This makes it particularly well suited for rubber gloves and bandages. Moreover, natural rubber latex articles are an effective barrier to the transmission of bacterial and viral pathogens which further enhances their medical utility.

The ability to maintain these normally occurring beneficial properties of natural rubber latex is one of the primary strengths of the present invention. In contrast to prior art processes which may change the chemical structure of the natural rubber latex itself, the present invention targets and alters only the antigenicity of the allergenic components of the material. In addition to maintaining the physical and performance advantages of the different articles and devices so produced, there is an associated practical advantage that results as well. Because the underlying formulation of the natural rubber latex remains unchanged by the present invention, additional clinical data should not be required to obtain regulatory approval prior to the medical use of the claimed methods, materials, and devices. This feature alone will significantly reduce the expenses normally associated with the production of new or improved medical materials and of the devices which incorporate them.

As previously discussed, the present invention is able to produce hypoallergenic natural rubber latex articles exhibiting these beneficial features and advantages without major modification to normal manufacturing techniques. Of these, one of the most common latex manufacturing procedures is the dip-forming process. In this procedure, an article forming mandrel is simply coated with the latex emulsion by dipping the mandrel into a latex emulsion bath or tank followed by rinsing and drying/curing steps prior to removal of the latex article from the mandrel.

Considerable effort is devoted to the design and manufacture of the article forming mandrels. Typically constructed of stainless steel or ceramic, dip-forming mandrels must be accurately dimensioned and shaped to produce the appropriately sized and configured latex articles for their intended purposes. Most often, the mandrels are incorporated into automated mass production techniques involving repeated dipping and removal of the mandrels into and out of pre-treatment, emulsion, and rinsing baths in conjunction with oven drying. Thus, they must be sufficient to withstand repeated use and elevated temperatures.

In some circumstances, the dip-formed latex articles are "inverted" or turned inside out to peel or remove them from the forming mandrels. The production of rubber gloves and condoms commonly utilizes such an inversion step for removal so that the inner surface of the finished article is actually the outer surface of the originally dip-formed product. Conversely, inflation balloons are not inverted for removal from the article forming mandrel. Preferential stretching properties produced by the dip-forming process require that the balloons be removed without being turned inside out. Of equal importance, it is not uncommon to use release agents on the forming mandrels which may become embedded in the latex article surfaces originally contacting the mandrel during dip-forming. Interestingly, even though dip-formed latex articles may or may not be inverted during their manufacturing processes, it is most commonly the original outer latex surfaces produced directly on the article forming mandrels which ultimately come into contact with a user's or patient's tissue. In the exemplary embodiments of the present invention discussed herein, it is this outer surface that is treated during the manufacturing process to reduce its allergenicity. However, it should be emphasized that the present invention is equally applicable to treatment of the inner or both surfaces of the latex articles.

Broadly speaking, the present invention accomplishes this objective through a very few, simple steps incorporated into dip-forming or other manufacturing protocols at the appropriate or preferred stages. In its broadest aspect, the present invention induces the normally occurring natural rubber latex antigenic components to bloom onto the article surface intended to contact tissue. In the dip-forming process this can be accomplished by providing a natural rubber latex emulsion which includes its normal compliment of antigenic components. As previously discussed, these antigenic components are comprised of a wide variety of naturally occurring biopolymers including proteinaceous and non-proteinaceous compounds. These surfactant and detergent-like biopolymers typically incorporate a number of reactive functional groups along their protein or polymer backbones. For example, $NH_2$, —OH, and =S are some of the functional groups that provide reaction or docking sites for the subsequently applied screening reagents of the present invention. While in some cases it may be possible to add the screening reagents to the natural rubber latex emulsion as a preliminary manufacturing step, this may not be desirable if the preservation of antioxidant compounds and preservatives is desired. Many prior art treatment protocols exhibit this drawback. However, by selecting screening reagents with appropriate partition coefficients and reactivity it is possible to avoid undesirable interaction with antioxidant and preservative compounds by inducing antigenic component blooming at the emulsion interfaces.

The present invention overcomes the problems normally associated with pretreatment of natural rubber latex emulsions by inducing the blooming of the antigenic components, preferable onto and adjacent to the surfaces intended to come into contact with a patient's tissue. This can be accomplished directly in the emulsion as discussed above as well as during the formation of the latex article from the natural rubber latex emulsion. For example, where the latex article is formed by dipping an article forming mandrel into the latex emulsion, blooming can be induced by coagulating the latex emulsion into a gel on the surface of the dipped article forming mandrel.

Coagulation of the latex emulsion displaces the aqueous carrier solution toward the exposed surface of the coagulated gel. In accordance with the teachings of the present invention, as the emulsion coagulates, the antigenic component concentration and associated phase differential migrates toward the exposed surface carrying the water soluble antigenic components with it. This results in their loose incorporation to the coagulated gel structure at a position onto or adjacent to the exposed gel surface. On a molecular level, this exposed surface is highly convoluted and loosely covered with the exposed antigenic regions of the loosely embedded, bloomed antigenic surfactant components. As a result, the bloomed antigenic components are presented on the tissue contacting surface of the formed latex article in a manner making them individually susceptible to chemical screening treatment without affecting the underlying base polymer of the natural rubber latex gel.

Chemically treating the bloomed antigenic components with one or more screening reagents sequesters the antigenic regions of these loosely bound exposed biopolymers rendering them virtually inert to the body's immune system during subsequent tissue contacting events. It is this screening or covering up of the antigenic regions that reduces the allergenicity of the natural rubber latex articles of the present invention. It should be emphasized that this is not a simple coating process as practiced in the prior art. The present invention actively covers the allergenic regions of the antigenic components on an individual molecular basis and does so well into the interior of the convoluted surface of the material without coating the material surface with films, polymer grafts, or the like.

Similarly, chemical treatment with the screening reagent is not an enzyme treatment which digests one protein with another nor is it a simple washing process which solubilizes and removes antigenic components. Rather, the method of the present invention is more analogous to the chemical tanning or "fixing" of naturally occurring tissues, but with the added focus of sequestering antigenic regions rather than merely cross-linking proteinaceous tissues to prevent mechanical degradation.

The chemical treating step of the present invention is also a simple process. It can be accomplished by dipping, soaking, spraying, or any analogous technique that allows the screening reagent to engage the bloomed antigenic components under appropriate reaction conditions for a sufficient period of time to allow reaction to progress. In the exemplary dip-forming methodology discussed herein, this can be accomplished through the provision of a simple aqueous or non-aqueous dipping bath containing an effective concentration of one or more screening reagents under appropriately mild reaction conditions of temperature and pH. The formed latex article having bloomed antigenic components is simply immersed in the treatment bath for the appropriate period of time, removed and rinsed in a separate rinsing step to remove unreacted screening reagent and other soluble components.

The treating procedure is equally applicable to cured latex emulsions as well as the emulsions and coagulated gels previously discussed. In these alternative embodiments, the gelled latex emulsions having bloomed antigenic components on their surfaces are cured in a normal manner involving drying and/or heat. Curing will bind the bloomed antigenic components more tightly to the convoluted molecular surface and may reduce the ability of an aqueous treating bath to penetrate as deeply into the latex structure as can be accomplished with a non-aqueous bath or by treating the emulsion or coagulated gel. Exemplary non-aqueous baths include organic solvents such as alcohols, betones, esters, and the like as known in the art and as compatible with the reactions and reaction conditions. Nonetheless, even with such modifications and alternatives allergenicity of the cured latex article surface is significantly reduced through chemically treating the bloomed antigenic components in accordance with the teachings of the present invention.

In any case, relatively mild reaction conditions are suitable for practicing the present invention. Mild conditions help to prevent the interaction of the screening reagent with the base natural rubber latex polymer presenting the bloomed antigenic components on its surface. As an added benefit, mild reaction conditions can be readily incorporated into existing manufacturing processes. Exemplary mild reaction conditions include temperatures ranging from approximately 20° C. to 100° C. Preferred temperatures may be on the order of 60° C. to 80° C. Thus, chemical treatment reaction solutions or baths can be produced and maintained inexpensively at room temperature or slightly above. This will effectively drive the screening reaction without affecting the antioxidants which may be present in the latex emulsion or the latex itself.

Similarly, the reaction solutions or treatment baths should have a pH sufficiently high to induce reaction between the target antigenic component binding regions and the screening reagents without opening up the vinyl bonds of the associated natural rubber base polymer. Exemplary pH ranges for practicing the present invention include mildly basic treatment conditions of 9 pH units to 12 pH units. Preferred pHs may be on the order of 10.5.

Under these relatively mild reaction conditions it is appropriate to leave the screening reagents in contact with the bloomed article surface for periods ranging from 1 minute to 30 minutes. The exact period can be determined experimentally with little effort in order to allow the screening reaction to proceed to an effective end point. Shorter exposure periods are preferred as they produce minimal impact or delay an normal manufacturing processes. Accordingly, reaction time periods ranging from 3 minutes to 10 minutes may be preferred.

The screening reagents must be chemical compounds which react with the antigenic components under the relatively mild conditions discussed above. Also, they should not affect the biocompatibility or molecular structure of the base rubber polymer and, preferably, be relatively non-toxic. Selection of the reagents and reaction conditions in accordance with the teachings of the present invention will accomplish these objectives. Exemplary chemical screening agents useful for the practice of multifunctional and the present invention include a variety of difunctional reagents such as diepoxies, dialdehydes, dienes, bismalimides, and diisocyanates. Specific exemplary screening agents within these classifications include ethylene glycol diglycidyl ether, glutaric dialdehyde, 1,4-butanediol diglycidyl ether, and divinyl sulfone. Those skilled in the art will appreciate that any similarly functional compounds may be utilized as screening reagents consistent with the teachings of the present invention.

Additionally, modifying any of these reagents with reactive groups and side chains is also contemplated as being within the scope of the present invention. For example, adding detergent-like side chains to the reagents can be used to modify their partition coefficients. Alternatively, adding bulky side chains may enhance their screening effectiveness following reaction. Substituting oligimers and low molecular weight polymers containing the appropriate functional groups and side chains may also be used for the screening reagents. For example, the polyepoxy compound formed from polyvinyl alcohol and epichlorhydrin may be an effective screening reagent.

Depending upon the screening reagent or reagents being used, the chemical treatment may be conducted under dry, aqueous, or non-aqueous conditions. Aqueous conditions are preferred as they are readily compatible with the natural occurring latex emulsions and are considerably easier to handle. Their relatively low expense and toxicity are additional benefits. The concentration of screening reagent will also depend on the type of solution and the reagent itself. Exemplary screening reagent concentrations believed to be effective range from 0.1 wt % to 10 wt %, though greater or lesser concentrations are contemplated as being within the scope of the present invention. Lower concentrations may slow the reaction rate and resultant production process whereas higher concentrations may be more expensive and difficult to deal with without producing a concomitant production advantage. Accordingly, the exemplary concentration ranges are believed to be best and need only be modified to accommodate circumstances or chemistry.

Further refinements of the present invention enable the skilled practitioner to fine tune the hydrophobic/hydrophilic character of the screening reagents to more closely match those of the target antigenic regions presented by the bloomed antigenic components. This helps to focus the reactions on the target sites and away from the underlying base polymer. Specifically, as those skilled in the art will appreciate, because the bloomed antigenic components are bound within the emulsion interface, surrounding latex gel, or polymer, the projecting molecular elements will exhibit increasing hydrophilicity (water compatibility) as they extend away from the interface or article surface. Those molecular components closest to the surface, or embedded within the latex emulsion or article adjacent to the interface or surface, will be considerably more hydrophobic (water repelling). By fine tuning or harmonizing the hydrophobic/ hydrophilic character of the screening reagent utilized, the present invention can effectively target these specifically hydrophobic or hydrophilic antigenic regions on the bloomed antigenic components.

Through experiment, it has been determined that the more hydrophobic or more hydrophilic screening reagents may be less effective under some circumstances than screening reagents that exhibit both mildly hydrophilic and mildly hydrophobic characteristics. Ethylene glycol diglycidyl ether and glutaric dialdehyde are examples of screening reagents having partition coefficients midway between hydrophobicity and hydrophilicity. It is believed that these reagents target antigenic regions closely adjacent to the bloomed latex surfaces rather than the antigenic regions projecting out into the surrounding environments or deeply embedded in the underlying base polymer or emulsion interface. Experimental evidence indicates that this may be the most effective target for reducing allergenicity of natural rubber latex materials.

With this understanding in mind, an exemplary natural rubber latex manufacturing process incorporating the teachings of the present invention can be practiced as follows. In this embodiment of the present invention, treatment with the screening reagent will occur during the gel stage as this will allow easy diffusion of the screening reagent into the hydrated gel material. Moreover, there is little or no interaction between the screening reagent and any vulcanizing or antioxidizing chemicals present in the latex emulsion at this stage by virtue of the mild reaction conditions and the appropriately selected screening reagents.

Exemplifying the ready applicability of the present invention to existing production techniques, the first step in the manufacturing process involves compounding a natural rubber latex emulsion using standard formulations and techniques. Typically, a raw natural rubber latex aqueous emulsion is pretreated with a variety of vulcanizing, cross-linking and antioxidant compounds including zinc oxide, sulfur, amines, thiols and other antioxidants and accelerators. This combination of materials is heated and stirred under seal for a period of hours to produce a raw material suitable for dip-forming or other manufacturing processes.

In the standard dip-forming procedure, the next step in the process involves dipping an article forming mandrel having the desired configuration into a standard coagulant system followed by drying. For example, a bead blasted stainless steel forming mandrel may be dipped in a solution of alcohol and $Ca(NO_3)_2$. In some manufacturing techniques, the dipping mandrel is "straight dipped" without a coagulating pretreatment. In either approach, the mandrel is then dipped into the natural rubber latex compound (which may include stabilizers and other components as discussed above) and removed with a thin coating of adhered latex emulsion.

After a brief period of time in air to allow the dipped latex emulsion to congeal and induce the surface blooming of the antigenic components, the dipped, latex coated forming mandrel is rinsed in a water bath to remove any easily soluble compounds and extract any ions and the like from the surface of the gelled emulsion. This produces a congealed, gelatinous latex article having a very high surface area including the entrapped bloomed antigenic components with exposed hydrophilic and antigenic regions. As those skilled in the art will appreciate, washing will only remove approximately 30% of these naturally occurring surfactant molecules. Thus, a significant proportion of those antigenic components originally present in the latex emulsion remain at or near the bloomed surface of the latex gel.

Further illustrating how easily the present invention is integrated into existing manufacturing technology, chemical treatment of the bloomed antigenic components can be accomplished at this stage by simply dipping the rinsed, latex coated forming mandrel in a treatment bath containing, for example, 5 wt % ethylene glycol diglycidyl ether in a buffered solution at pH 10.5 at a temperature between 50° C. and 80° C. for approximately 3 to 15 minutes. An additional washing step in water at, for example, 60° C. for 20 minutes removes any unreacted screening reagent along with soluble ions, proteins, and other components not removed in the first rinse. The treated article is then dried and cured to its final form utilizing normal manufacturing procedures such as 90 minutes in a 90° C. oven followed by removal from the dipping mandrel. This produces a natural rubber latex article having normal chemical, physical, and mechanical properties with a tissue contacting surface including embedded bloomed antigenic components that are effectively screened from allergic response by the screening reagent covering their antigenic regions.

Alternatively, the foregoing dip-forming procedure for manufacturing natural rubber latex articles and membranes can be practiced as usual with the treatment step following curing of the article. In this alternative procedure, the cured or finished article with the bloomed antigenic components presented on its surface is treated with the same treatment solution bath as before and allowed to dry either prior to or after removal from the forming mandrel. Either of these alternative manufacturing protocols may be utilized to practice the present invention and non-aqueous treatment baths may be utilized where appropriate.

It should be emphasized again that these protocols are exemplary only and are intended to illustrate the ability of the present invention to integrate into existing manufacturing procedures. Alternative manufacturing processes known in the art and not discussed herein are equally suitable for integration with the teachings of the present invention to produce hypoallergenic natural rubber latex articles as disclosed. For example, the raw latex emulsion may be treated with one or more screening reagents having partition coefficients sufficient to induce antigenic component blooming at the emulsion interfaces to treat the reactive sites. Alternatively, the coagulant system applied to the forming mandrel may be formulated to include one or more screening reagents. This will allow the inner surface of the gelled emulsion to be treated, and does not prevent subsequent treatment of the outer gel surface. Similarly, the outer surface of the latex article can be treated as discussed above prior to inversion of the article and treatment of the inner surface through dipping, spraying, or other treatment. If desired, the screening reagents can be incorporated into powder-free release coating or donning coating formulations which are typically applied to many latex articles as known in the art. It is even contemplated as being within the cope of the present invention to incorporate one or more screening reagents into actual polymer coatings which can be applied to the finished latex articles to simultaneously coat and sequester antigenic components. The only significant limitation is to the broad based applicability of the teachings of the present invention to most phases of article forming technology are potentially undesirable chemical reactions which can be eliminated through routine experimentation by those skilled in the art.

To demonstrate the reduced allergenicity of the latex articles produced in accordance with the teachings of the present invention, a competitive inhibition assay was conducted on a number of exemplary latex membranes and balloons. As known in the art, under appropriate experimental conditions, a standard allergenicity curve can be developed relating the quantity of latex allergenic component added to several human serum samples with the associated percent inhibition produced. The quantity of latex allergen present in unknown extracts can then be measured by comparing the inhibition produced by the unknown to the standard curve. For example, assays can be constructed to measure the quantity of human immunoglobulin (an immunoreactive molecule), such as $Ig_E$, binding to the allergenic components of latex. If a sample of human serum containing anti-latex $Ig_E$ is mixed and incubated with a solution containing latex allergens, a portion of the anti-latex $Ig_E$ will bind to the latex allergenic components in the solution. If this sample is then assayed, it is possible to determine how much the amount of latex specific $Ig_E$ has been reduced by reaction with the anti-latex antibody. This reduction in detectable $Ig_E$ can be expressed as a percent inhibition when a control sample is similarly treated with a solution that does not contain allergenic components and subsequently tested for $Ig_E$ in the same manner.

Those skilled in the art of determining allergenicity will appreciate that the presently utilized competitive inhibition assays give widely varying results depending upon the types of materials tested and the protocols utilized. As a result, it is not possible to directly relate allergenicity between various samples. However, utilizing careful assay techniques and appropriate controls, it is possible to measure relative allergenicity and to control for the widely varying test results.

Accordingly, in order to quantify and verify the reduction in allergenicity obtained through utilization of the present invention, competitive inhibition assays were conducted analogous to those reportedly being developed by the United States Federal Food and Drug Administration for measuring the allergenicity of latex gloves. Appropriate comparative controls were put into place to contrast untreated natural rubber latex membranes and balloons with those treated in accordance with the teachings of the present invention to quantify the reduction in allergenicity produced. In the following examples, the allergenicity is expressed as a −log ratio. Thus, log ratio numbers close to or below zero are indicative of very small or inferior reductions in allergenicity between treated versus control articles. Log ratio numbers of 1.0 equal a 90% reduction in allergenicity. Log ratios of 2.0 equal a 99.0% reduction in allergenicity and so on.

In each of the following nonlimiting examples, the same testing protocol was used to determine allergenicity. Natural rubber latex articles were treated in accordance with the teachings of the present invention at either the coagulated natural latex gel stage or at the cured latex membrane stage. The principal differences between the various exemplary treatment protocols are the screening reagents utilized and the modifications of the different treatment conditions as identified by the column headings.

EXAMPLE 1

Divinyl Sulfone Screening Reagent
Treatment of Cured Latex Membrane

| Concentration (wt %) | Time (Minutes) | Temperature (Degrees C.) | pH (pH Units) | Allergenicity (−Log Ratio) |
|---|---|---|---|---|
| 3 | 10 | 60 | 9.5 | −0.25 |
| 10 | 3 | 60 | 9.5 | −0.32 |
| 10 | 30 | 60 | 9.5 | 0.56 |

Example 1 is indicative of a small improvement in allergenicity, at best, over an untreated control sample.

EXAMPLE 2

Glutaric Dialdehyde
Coagulated Natural Latex Gel

| Concentration (wt %) | Time (Minutes) | Temperature (Degrees C.) | pH (pH Units) | Allergenicity (−Log Ratio) |
|---|---|---|---|---|
| 0.3 | 10 | 60 | 9.5 | * |
| 0.3 | 3 | 60 | 9.5 | 0.6 |
| 0.3 | 30 | 60 | 9.5 | * |
| 0.3 | 1 | 60 | 9.5 | 0.28 |
| 1 | 30 | 60 | 9.5 | * |
| 1 | 10 | 60 | 9.5 | * |
| 1 | 3 | 60 | 9.5 | 1.52 |
| 1 | 1 | 60 | 9.5 | 1.52 |
| 3 | 30 | 60 | 9.5 | * |
| 3 | 10 | 60 | 9.5 | * |
| 3 | 3 | 60 | 9.5 | 1.15 |
| 3 | 1 | 60 | 9.5 | 0.55 |
| 10 | 1 | 60 | 9.5 | >1.7 |
| 10 | 3 | 60 | 9.5 | >1.22 |
| 10 | 10 | 60 | 9.5 | 0.49 |
| 10 | 30 | 60 | 9.5 | >0 |

* Samples not submitted for analysis.
Note:
Total leaching time for experimental balloons was longer than for control balloons.

Example 2 is indicative of a significant improvement in allergenicity obtained at the gel stage relative to untreated control articles. Variations in assay results make it difficult to determine the optimum experimental conditions with this initial analysis. Additionally, the screening reagent is believed to have interacted with ammonia present in the latex emulsion.

EXAMPLE 3

Glutaric Dialdehyde
Treatment of Cured Latex Membrane

| Concentration (wt %) | Time (Minutes) | Temperature (Degrees C.) | pH (pH Units) | Allergenicity (−Log Ratio) |
|---|---|---|---|---|
| 3 | 10 | 60 | 9.5 | 1.66 |
| 10 | 3 | 60 | 9.5 | 1.16 |
| 10 | 30 | 60 | 9.5 | 1.23 |

As with Example 2, treatment of the latex articles with the higher concentrations of the same reagent, but at the dried or cured stage, produced equally significant reductions in allergenicity. Additionally, treatment at this stage in the manufacturing process eliminated the ammonia reaction that may have occurred with the screening reagent at the gel stage.

EXAMPLE 4

Denacol EX-313
Treatment of Coagulated Natural Latex Gel

| Concentration (wt %) | Time (Minutes) | Temperature (Degrees C.) | pH (pH Units) | Allergenicity (−Log Ratio) |
|---|---|---|---|---|
| 0.3 | 30 | 60 | 9.5 | 2 |
| 1 | 10 | 60 | 9.5 | 0.72 |
| 3 | 3 | 60 | 9.5 | −0.021 |

Note:
Total leaching time for experimental samples was longer than for control samples.

Example 4 is indicative of widely variable reductions in allergenicity that may actually be illustrating limitations with the competitive inhibition assay itself. Alternatively, increased reaction duration apparently increased the reduction in allergenicity obtained with this screening reagent treatment at the gel stage.

EXAMPLE 5

1,4-Butanediol Diglycidyl Ether
Treatment of Coagulated Natural Latex Gel

| Concentration (wt %) | Time (Minutes) | Temperature (Degrees C.) | pH (pH Units) | Allergenicity (−Log Ratio) |
|---|---|---|---|---|
| 5 | 1 | 60 | 10.5 | 0.37 |
| 5 | 5 | 60 | 10.5 | 1.4 |
| 10 | 1 | 60 | 10.5 | 0.49 |
| 10 | 5 | 60 | 10.5 | 1.7 |

Example 5 is illustrative of a number of different aspects of the present invention. First, diepoxy screening reagents may need higher pHs to be effective. More importantly, the reduction in allergenicity achieved utilizing these reagents in accordance with the teachings of the present invention are significantly higher and relatively more consistent in view of the known variability of standard inhibition assay results. Moreover, the 1,4-butanediol diglycidyl ether screening reagent is more hydrophobic than the relatively hydrophilic screening reagents utilized in the previous examples. This indicates that the target antigenic regions on the bloomed antigenic components are closer to the surface of the latex article. Screening these areas produces a more dramatic reduction in allergenicity.

EXAMPLE 6

Ethylene Glycol Diglycidyl Ether
Treatment of Cured Latex Membrane

| Concentration (wt %) | Time (Minutes) | Temperature (Degrees C.) | pH (pH Units) | Allergenicity (−Log Ratio) |
|---|---|---|---|---|
| 3 | 10 | 60 | 9.5 | 1.61 |
| 10 | 3 | 60 | 9.5 | >2.25 |
| 10 | 30 | 60 | 9.5 | >2.25 |

Note:
">" indicates assay results below the minimum detectable level.

Example 6 is illustrative of equally significant reductions in allergenicity obtained with ethylene glycol diglycidyl ether, a screening reagent exhibiting both mildly hydrophobic and mildly hydrophilic character analogous to that of 1,4-butanediol diglycidyl ether.

EXAMPLE 7

Ethylene Glycol Diglycidyl Ether
Treatment of Coagulated Natural Latex Gel

| Concentration (wt %) | Time (Minutes) | Temperature (Degrees C.) | pH (pH Units) | Allergenicity (−Log Ratio) |
|---|---|---|---|---|
| 0.3 | 30 | 60 | 10.5 | * |
| 1 | 10 | 60 | 10.5 | * |
| 3 | 3 | 60 | 10.5 | 0.19 |
| 10 | 1 | 60 | 10.5 | 2 |
| 10 | 3 | 60 | 10.5 | 2.52 |
| 10 | 10 | 60 | 10.5 | 2.7 |
| 3 | 10 | 60 | 10.5 | 2.52 |
| 3 | 30 | 60 | 10.5 | * |
| 3 | 1 | 60 | 10.5 | −1.1 |
| 0.3 | 10 | 60 | 10.5 | * |
| 0.3 | 3 | 60 | 10.5 | −0.14 |
| 0.3 | 1 | 60 | 10.5 | −.1 |

* Samples not submitted for analysis.
Note:
Total leaching time for experimental samples was longer than for control samples.

Note: Total leaching time for experimental samples was longer than for control samples.

Example 7 illustrates that equally effective reductions in allergenicity were obtained with ethylene glycol diglycidyl ether screening reagent treatment at the coagulated latex gel stage under differing treatment conditions.

EXAMPLE 8

Ethylene Glycol Diglycidyl Ether
Treatment of coagulated Natural Latex Gel

| Concentration (wt %) | Time (Minutes) | Temperature (Degrees C.) | pH (pH Units) | Allergenicity (−Log Ratio) |
|---|---|---|---|---|
| 0.3 | 10 | 60 | 10.5 | −0.23 |
| 1 | 10 | 60 | 10.5 | −0.13 |
| 1 | 3 | 60 | 10.5 | −0.62 |
| 1 | 30 | 60 | 10.5 | 1.7 |
| 1 | 1 | 60 | 10.5 | −0.32 |
| 3 | 10 | 60 | 10.5 | 2.7 |
| 10 | 10 | 60 | 10.5 | 2.4 |
| 3.0 | 3.0 | 60 | 10.5 | >1.3 |
| 3.0 | 5.0 | 60 | 10.5 | >1.4 |
| 3.0 | 8.0 | 60 | 10.5 | >0.96 |
| 4.0 | 3.0 | 60 | 10.5 | >1.7 |
| 4.0 | 5.0 | 60 | 10.5 | 0.48 |
| 4.0 | 8.0 | 60 | 10.5 | 1.05 |
| 8.0 | 3.0 | 60 | 10.5 | 1.7 |
| 8.0 | 5.0 | 60 | 10.5 | >1.52 |
| 8.0 | 8.0 | 60 | 10.5 | >1.4 |
| 3.0 | 8.0 | 70 | 9.5 | >0.8 |
| 3.0 | 3.0 | 60 | 9.5 | 0.62 |
| 3.0 | 8.0 | 60 | 10.5 | 0.41 |
| 3.0 | 3.0 | 70 | 10.5 | −0.49 |
| 8.0 | 8.0 | 60 | 9.5 | >2.0 |
| 8.0 | 3.0 | 70 | 9.5 | 1.7 |
| 8.0 | 8.0 | 60 | 9.5 | 1.7 |
| 8.0 | 3.0 | 60 | 10.5 | −0.14 |
| 8.0 | 8.0 | 70 | 10.5 | 0.92 |
| 8.0 | 3.0 | 60 | 10.5 | 0.19 |
| 8.0 | 8.0 | 70 | 10.5 | 0.59 |
| 5.0 | 5.0 | 60 | 10.5 | >1.05 |
| 5.0 | 5.0 | 50 | 11.5 | >1.40 |
| 5.0 | 5.0 | 50 | 10.5 | >1.15 |
| 5.0 | 5.0 | 60 | 11.5 | >1.52 |
| 5.0 | 5.0 | 50 | 11.5 | >1.40 |
| 5.0 | 5.0 | 60 | 10.5 | >1.52 |
| 5.0 | 5.0 | 60 | 11.5 | >1.52 |
| 5.0 | 5.0 | 50 | 11.5 | 1.22 |

Example 8 is illustrative of the effectiveness of ethylene glycol diglycidyl ether screening reagent applied at the gel stage under various reaction conditions of concentration, time, temperature, and pH. As before, significant reductions in allergenicity versus untreated controls were obtained with this screening reagent. The limitation of the assay are also evidenced by the divergent results at similar treatment conditions.

In closing, it should be understood that the embodiments of the present invention disclosed herein are illustrative of the principles of the present invention, and that other modifications may be employed which are within the scope thereof. For example, natural rubber latex sap or emulsions obtained from alternative sources may be employed. Alternative reagents and associated treatment steps and conditions also may be employed within the scope of the present invention. Accordingly, the present invention is not limited to that precisely as disclosed and described, and is limited only by the appended claims.

What is claimed is:

1. A method for the production of a hypoallergenic natural rubber latex article having normal physical, mechanical, and chemical properties and at least one tissue contacting surface exhibiting reduced allergenicity, said method comprising the steps of:

providing a natural rubber latex emulsion including antigenic components;

forming a latex article from said emulsion, said article having at least one surface intended to contact tissue and having at least one exposed surface;

inducing the blooming of said antigenic components onto and adjacent to said at least one surface by coagulating the latex emulsion into a gel on the surface of the dipped article and displacing said antigenic components of said gelled latex emulsion toward the exposed surface of said gel; and chemically treating said bloomed antigenic components with at least one screening reagent to sequester the antigenic regions of the said bloomed antigenic components by dipping said bloomed gelled latex emulsion into a treating bath containing an effective concentration of said at least one screening reagent under mild conditions of temperature and pH for a sufficient period of time to react said at least one screening reagent with said bloomed antigenic components, whereby said screening reagent selectively chemically interacts in a linking reaction with the antigenic regions of said bloomed antigenic components.

2. The method of claim 1 wherein said natural rubber latex article is formed through the additional steps of dipping an article forming mandrel into said latex emulsion; and removing said dipped article forming mandrel from said emulsion.

3. The method of claim 2 further including the step of rinsing said treated gel to remove unreacted screening reagent and any other soluble components.

4. The method of claim 3 wherein said effective concentration of said at least one screening reagent ranges from 0.1 wt % to 10 wt %.

5. The method of claim 3 wherein said temperature of said treating bath ranges from 20° C. to 100° C.

6. The method of claim 3 wherein said pH of said treating bath ranges from 9 to 12.

7. The method of claim 3 wherein said sufficient period of time ranges from 1 minute to 30 minutes.

8. The method of claim 1 wherein said at least one screening reagent is a multifunctional agent.

9. The method of claim 8 wherein said multi-functional agent is a difunctional agent selected from the group consisting of diepoxies, dialdehydes, dienes, diisocyanates, and bismalimides.

10. The method of claim 1 wherein said at least one screening reagent is a difunctional agent selected from the group consisting of ethylene glycol diglycidyl ether, 1,4-butanediol diglycidyl ether, glutaric dialdehyde, and divinyl sulfone.

11. The method of claim 2 further comprising the additional step of curing said gelled latex emulsion prior to chemically treating said bloomed antigenic components with said at least one screening reagent.

12. The method of claim 1 further comprising the additional step of identifying at least one target antigenic region of said bloomed antigenic components; and harmonizing the hydrophobic/hydrophilic character of said at least one screening reagent to the hydrophobic/hydrophilic character of said at least one target antigenic region.

13. The method of claim 12, wherein said at least one screening reagent exhibits a hydrophobic/hydrophilic character that is both mildly hydrophobic and mildly hydrophilic.

14. The method of claim 12 wherein said at least one screening reagent is ethylene glycol diglycidyl ether.

15. A natural rubber latex article having normal physical, mechanical, and chemical properties, and at least one tissue contacting surface exhibiting reduced allergenicity, said article produced through the steps of:

inducing the blooming of the natural rubber latex antigenic components onto and adjacent to said at least one tissue contacting surface of said article by coagulating the latex emulsion into a gel on said surface of the dipped article and displacing said antigenic components of said gelled latex emulsion toward said surface of said gel; and chemically treating said bloomed antigenic components with at least one screening reagent to sequester the antigenic regions of the said bloomed antigenic components by dipping said bloomed gelled latex emulsion into a treating bath containing an effective concentration of said at least one screening reagent under mild conditions of temperature and pH for a sufficient period of time to react said at least one screening reagent with said bloomed antigenic components, whereby said screening reagent selectively chemically interacts in a linking reaction with the antigenic regions of said bloomed antigenic components.

16. The natural rubber latex article of claim 15 wherein said natural rubber latex is gelled.

17. The natural rubber latex article of claim 15 wherein said gelled natural rubber latex is cured.

18. The natural rubber latex article of claim 15 comprising a glove.

19. The natural rubber latex article of claim 15 comprising a condom.

20. The natural rubber latex article of claim 15 comprising an inflatable balloon.

* * * * *